United States Patent [19]

McGinnis

[11] Patent Number: 4,744,358

[45] Date of Patent: May 17, 1988

[54] ENDOTRACHEAL TUBE HOLDER

[76] Inventor: Gerald E. McGinnis, 131 Kelvington Dr., Monroeville, Allegheny County, Pa. 15146

[21] Appl. No.: 571,785

[22] Filed: Jan. 18, 1984

[51] Int. Cl.$^4$ .............................................. A61M 25/62
[52] U.S. Cl. ......................... 128/207.17; 128/DIG. 26
[58] Field of Search .................. 128/DIG. 26, 207.14, 128/207.15, 207.17, 207.18, 200.26, 203.18, 206.27, 207.11, 97, 163, DIG. 15; 24/16 PB, 17 A, 17 AB; 604/179, 174, 180, 416–419, 183; 2/173, 176, 205

[56] References Cited

U.S. PATENT DOCUMENTS

| D. 283,158 | 3/1986 | Jackson | 128/207.14 |
| 804,272 | 11/1908 | Schwartz | 128/207.18 |
| 2,292,568 | 8/1942 | Kanter et al. | 128/203.28 |
| 2,353,643 | 7/1944 | Bulbulian | 128/207.11 |
| 2,398,076 | 4/1946 | Bulbulian | 128/205.25 |
| 2,462,005 | 2/1949 | Schauweker | 128/207.11 |
| 3,025,525 | 3/1962 | Larson | 2/419 |
| 3,156,923 | 11/1964 | Timm | 2/419 |
| 3,714,668 | 2/1973 | Mirabella | 2/419 |
| 3,906,548 | 9/1975 | Kallis | 2/416 |
| 3,946,742 | 3/1976 | Eross | 128/207.17 |
| 3,955,570 | 5/1976 | Hutter, III | 128/201.23 |
| 3,976,080 | 8/1976 | Bornhorst et al. | 604/179 |
| 3,987,798 | 10/1976 | McGinnis | 128/207.17 |
| 4,055,773 | 10/1977 | Knab | 128/201.23 |
| 4,326,515 | 4/1982 | Shaffer et al. | 128/207.17 |
| 4,351,331 | 9/1982 | Gerey | 128/207.17 |

OTHER PUBLICATIONS

"Disposable Endotracheal Tube Holder", Hudson Oxygen Therapy Sales Co., Oct., 1980.

*Primary Examiner*—Edward M. Coven
*Assistant Examiner*—K. M. Reichle
*Attorney, Agent, or Firm*—Carothers & Carothers

[57] ABSTRACT

An endotracheal tube holder including an endotracheal tube platform portion having a clamp for clamping an endotracheal tube into a tube channel wherein the tube platform portion is supported with respect to the patient's head by the face plate frame secured to the face of a patient by a harness worn on the head of the patient. The endotracheal tube holder is secured with respect to the patient's face with portions thereof bearing on the upper and lower jaw portions of the patient's face.

6 Claims, 1 Drawing Sheet

U.S. Patent May 17, 1988 4,744,358
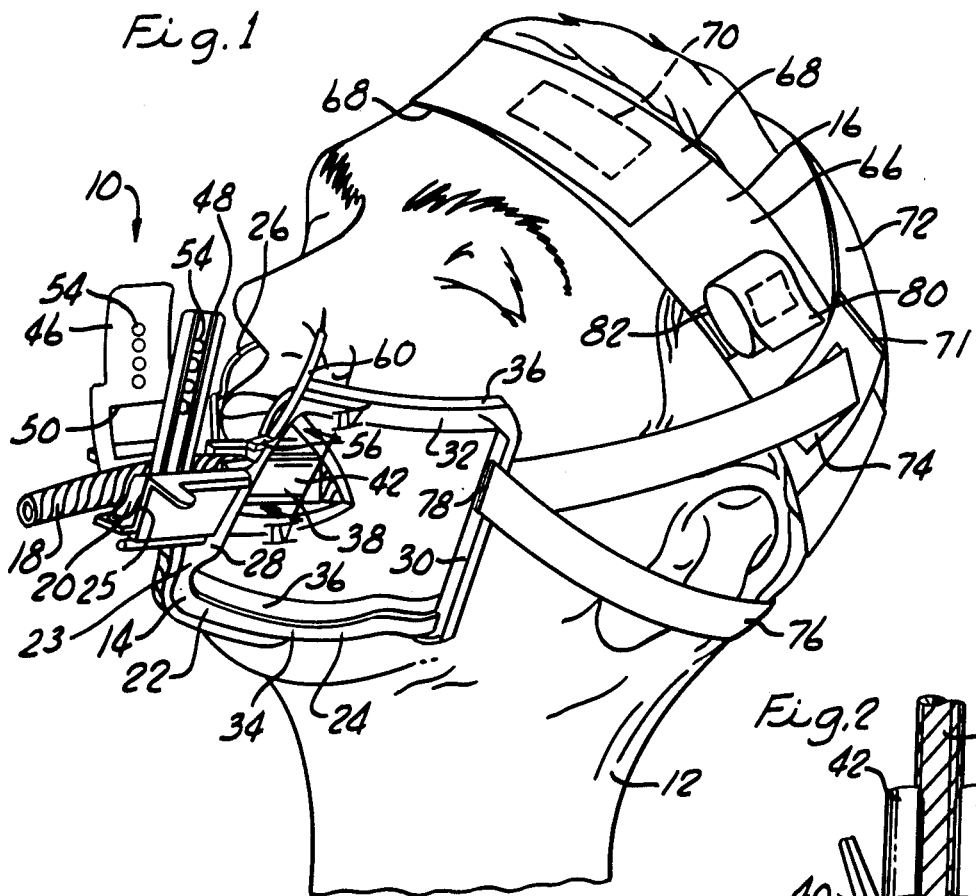

ENDOTRACHEAL TUBE HOLDER

BACKGROUND OF THE INVENTION

In the medical arts, it is well known to provide an endotracheal tube for use in ventilation of a patient for anesthesia, critical care, resuscitation and other procedures and care requirements commonly arising. The endotracheal tube is commonly connected to an external ventilating system and is inserted through the mouth of the patient into the trachea where an inflatable cuff on the tube is inflated with air pressure to seal the trachea.

In the prior art, the endotracheal tube commonly has been secured in place by any of a variety of means including adhesive tape applied to the facial area of the patient or an endotracheal tube holder which has often included a bite block that the patient grips in his teeth. The bite block serves the purpose of allowing the patient something to bite on in normal response to the insertion and presence of the tube in the throat. The prior art tube holders have also commonly included a tube lock means for securing the endotracheal tube in place with respect to the face plate of the tube holder. Typical of the prior art endotracheal tube holders are those disclosed in U.S. Pat. Nos. 2,908,269 and 3,774,616, for example.

The prior art of endotracheal tube holders has not been without significant deficiencies. For example, during nursing care, the run of tubing external to the patient commonly must be manipulated and this creates a tendency for the tubing within the trachea or airway of the patient to move also. Considerable discomfort may result for the conscious or semi-conscious patient as tube manipulation stimulates the patient's gag reflex. In response, the patient may choke or try to remove the tube from his airway. In addition, inadvertent movement of the tube during external manipulation thereof may result in trauma to the mucous membrane lining the upper regions of the throat. An additional problem associated with some prior tube holders is that oral care must be attended to without disturbing the tube or its securing system. This has not been possible with many prior tube holder systems.

Other problems evident in the prior art include the lack of a suitable means for securing the endotracheal tube with respect to the tube holder and for securing the tube holder to the patient's head. Preferably, there should be provided a simple and fast acting means for locking the tube with respect to the tube holder in a manner that angular movement of the external run of tube will not affect the angle of entry of the tube into the patient's mouth. An additional requirement to achieve this end is that suitable means be provided for securing the tube holder with respect to the patient's head in a firm but yet comfortable manner. This latter problem is of particular significance, as the patient often will have the tube in place in his airway for extended periods of time. The use of adhesive tape as a tube securing system, or of elastic bands which exert continuous pressure on the patient's skin, both have a tendency to traumatize the patient's skin and thereby create considerable additional patient discomfort over and above that of the tube itself.

SUMMARY OF THE INVENTION

The present invention contemplates an endotracheal tube holding and securing apparatus which alleviates the above and other problems. The present invention contemplates in one aspect thereof an endotracheal tube holder which includes a face plate structure in the form of an open framework which provides for improved ease of patient oral care and related nursing care, as well as improved patient comfort. The tube holder of the present invention also contemplates an improved non-elastic and non-adhesive harness system which not only secures the tube holder to the patient's face with a minimum of patient discomfort, but in addition provides means for guiding the external run of nasal tubes when such are to be used.

Accordingly, it is a general object of the present invention to provide an improved endotracheal tube holder apparatus.

Another object of the present invention is to provide an endotracheal tube holder which is secured to a patient's head in a manner to minimize shifting, bending and other movement of the tube in the patient's airway without resorting to adhesive tape, elastic bands, or other prior constraints.

Still another object of the present invention is to provide an endotracheal tube holder which offers access to the patient's mouth or normally required oral care and other nursing care without removal of the tube or tube holder.

BRIEF DESCRIPTION OF THE DRAWINGS

Other objects and advantages appear in the following description and claims.

The accompanying drawings show, for the purpose of exemplification without limiting the invention or the claims thereto, certain practical embodiments illustrating the principles of this invention wherein:

FIG. 1 is a perspective view of an endotracheal tube holder of the present invention as worn by a patient;

FIG. 2 is a top plan view of a fragmentary portion of the tube holder of FIG. 1 showing the operation of a tube gripping and locking means;

FIG. 3 is a view similar to FIG. 2 further showing operation of the tube gripping and locking means;

FIG. 4 is a fragmentary side elevation of the tube holder of FIG. 1 showing a nasal tube restraint means of the present invention has seen from line IV—IV of FIG. 1; and FIG. 5 is a fragmentary frontal elevation of the tube holder.

There is generally indicated at 10 in FIG. 1 an endotracheal tube holder apparatus constructed according to one presently preferred embodiment of the present invention and shown as it would be worn by a patient 12.

The endotracheal tube holder apparatus 10 includes a face plate assembly 14 which is secured to the face of patient 12 by a harness 16 which retains the face plate assembly 14 in the operative position thereof to support an endotracheal tube 18 which is separate from the tube holder 10. Face plate assembly 14 includes a central elongated tube platform portion 20, preferably of resiliently deformable material such as soft vinyl plastic, suitably affixed to a generally rigid, preferably unitary face plate framework 22 of molded plastic or the like, which includes respective left and right frame portions 24 and 26, only one of which frame portion is clearly shown in FIG. 1. It will be understood that face plate assembly 14 is generally symmetrical about the central vertical plane of the tube platform portion 20 along which tube 18 extends. Accordingly, the right side frame portion 26 is a mirror image of the left side frame portion 24. Therefore, only the frame portion 24 is described in detail hereinbelow, the other frame portion 26 being a mirror image of the one described.

The frame portion 24 includes a generally vertically extending elongated inner member 28, a generally vertically extending outer member 30 located laterally outward of inner member 28, and upper and lower laterally extending elongated members 32 and 34, respectively, which join the inner member 28 to outer member 30. Members 28, 30, 32 and 34 together comprise the frame portion 24 and are so profiled as to conform to the mouth, chin, cheek and jaw portions of a patient's face. Of course, standard or typical proportions are to be employed to achieve a universally comfortable fit of the face plate framework 22 on a typical patient to accommodate patients over a wide range of body sizes from small child to adult. Likewise, to accommodate commonly recognizable variations in facial structure, a variety of frame configurations may be provided, and the illustrative framework 22 of FIG. 1 therefore is not to be construed as a limitation on the present invention.

The open interior of frame portions 24 and 26 provides for improved ease of access to the patient's mouth for oral care and other nursing care as required.

To enhance patient comfort, some inner surfaces of the frame portions 24 and 26, for example, the inner surfaces of members 32 and 34, may be provided with a soft padding 36 of foam rubber or similar material affixed to the inner surface of members 32 and 34 as by gluing thereof. The padding 36 contacts the patient's face and bears upon the upper and lower jaws, respectively, to provide firm face plate assembly support. The padding 36 is sufficiently soft and flexible to accommodate variations between the profile of face plate framework 22 and the patient's jaw structure, thereby distributing contact forces and minimizing the trauma of extended periods of localized higher contact force.

Referring to FIGS. 1, 2 and 3, it will be seen that tube platform portion 20 includes an elongated platform of resilient material such as vinyl plastic as noted hereinabove, the platform 20 being elongated to extend both inwardly and outwardly of the patient's mouth. Adjacent an inner end portion 38 of platform 20 is a tube channel 40 extending within a bite block 42 upon which the patient may bite without damage or constriction of tube 18.

An outer end portion 44 of platform portion 20 includes a tube restraining means in the form of a pair of flexible tabs 46 and 48, preferably of soft vinyl plastic and integrally formed with tube platform portion 20. In FIG. 1, tabs 46 and 48 are shown disengaged from tube 18. One of the tabs, shown as tab 46, includes an aperture 50 through which the other tab 48 may be passed, such that the tabs 46 and 48 may overlap each other to secure tube 18 in place. The framework 22 includes laterally projecting prongs 52 located adjacent opposite sides of and laterally outward from tube platform portion 20, which prongs 52 interact with openings 54 formed in tabs 46 and 48 to secure tabs 46 and 48 in their operative positions. Specifically, as will be seen from FIG. 2, tab 48 has been passed over tube 18 and through aperture 50 and is engaged upon one of prongs 52 to clamp tube 18 in place within the tube channel 40 in tube platform portion 20. In FIG. 3, tab 46 has been passed in the opposite direction over tube 18 and is engaged upon the other prong 52, whereby tube 18 is firmly secured with respect to the face plate assembly 14. FIG. 5 also depicts the tabs 46 and 48 in their operative position clamping tube 18 in channel 40. The elongated form of tube platform portion 20 assures minimized angular movement of tube 18 at the patient's mouth in response to external tube manipulation, thus minimizing patient gag response, throat tissue trauma, and general patient discomfort.

FIG. 5 also illustrates the means in which the tube platform portion 20 is structured as a free standing member 19, preferably of soft vinyl plastic, secured adjacent a base portion 21 thereof at a central portion 23 of framework 22 formed at the junction of frame portions 24 and 26 whereat sidewall portions 25 of framework 22 project outwardly of frame 22. As member 19 projects upwardly from face plate 23 to receive tube 18 therein, the securement of tube 18 is afforded a degree of flexibility with respect to framework 22. The tube 18 generally will be more flexible than member 19 and no significant variation in the tube entry angle normally will occur. Additionally, tube receiving member 19 and the securing tabs 46 and 48, which preferably are integral therewith, are spaced laterally from the side wall portions 25 of framework 22, whereby, when tabs 46 and 48 are engaged on prongs 52, tube 18 is effectively suspended in a triangular configuration of tension members between suspension points corresponding to tabs 52 and base portion 21.

The choice of soft vinyl plastic for the tube platform portion 20 and for securing tabs 46 and 48 contributes significantly to the integrity of the tube securement, as the tube itself also commonly will be of soft vinyl plastic. Mutual contact of two surfaces of such vinyl plastic typically produces a surface friction which is the nature of an extremely tacky surface sticking that resists sliding of the tube 18 along the tube platform portion 20.

As shown in FIGS. 1 and 4, face plate assembly 14 also contemplates nasal tube guides 56 shown as a securing block 58 affixed suitably to member 28 of frame portion 24 as by gluing thereof, and including an elongated flexible tab 60 which may be passed in friction engagement through an opening 62 formed in block 58 to form a loop 64 which may have a nasal tube (not shown) passed therethrough for securing and guiding such nasal tube from the nostril and along the side of the patient's face. Preferably, one of the guides 56 is provided on each side of the face plate assembly 14, i.e., on each of frame portions 24 and 26.

The harness 16 which secures face plate assembly 14 to the patient's face for use includes a non-elastic headband 66 which generally horizontally encircles the patient's head and includes overlapping ends 68 having suitably, infinitely adjustable fastening means, such as hook and loop fasteners 70 (e.g., VELCRO ® fastener pads) whereby headband 66 may be adjusted to firmly and snuggly encompass the patient's head without applying undue pressure thereto. An overhead strap 72 is preferably permanently affixed to headband 66 to extend over the top of the patient's head generally from ear to ear. Like headband 66, strap 72 also has overlapping ends as at 71 and suitable fastening means such as VELCRO ® fastener pads to provide for a firm, snug and precise fit. The harness portions described hereinabove may generally be permanent and indefinitely reusable.

To secure face plate assembly 14 to the described harness portions, a fastener means such as a hook pad portion of a hook and loop fastener is provided as at 74, preferably adjacent the left and right side junctures of headband 66 with strap 72. A side strap 76 is attached to the fastener pad 74, shown in FIG. 1 on the left side of the patient's head, is then passed through an elongated slot 78 formed in the member 30 of frame portion 24 on the same side of the patient's head, thence around the back of the patient's neck or lower head, through an entirely similar slot in the frame portion 26, and then is attached to a fastener pad located adjacent the juncture of headband 66 and strap 72 on the right side of the harness 16.

The described harness 16 provides for firm securement of face plate assembly 14 in its use position by means of a precisely adjustable fit whereby the patient's head movement or external manipulation of the tube result in minimal disturbance of the tube in the patient's airway.

The side strap 76 may tend to become soiled in use and may be discarded and replaced with new strapping as required, and for this reason, side strap 76 is merely a piece of strap material cut from bulk to a suitable length and having no fastener means attached thereto for use.

Preferably, the material of the side strap 76 as well as that of headband 66 and overhead strap 72 is non-elastic, light in weight, highly flexible and compatible for securement to the hook pad portion of a hook and loop fastener. One such material consists of a foam backed fabric band having one surface which provides multitudinous fabric loops which are compatible for use with a hook pad portion of a hook and loop fastener and a reverse surface of resilient padding.

The pads which are used as fasteners in this invention, pads 70 and 74, for example, may be secured to one side of the material used for the harness 16 to accommodate infinite variability and flexibility of the harness size, thus providing for an extremely precise and comfortable fit for any patient.

Separate loops of such strap material, such as shown at 80 in FIG. 1, may be provided with hook fastener pads 82 for securing of the same to the harness 16 at any selected location to cooperate with nasal tube guides 56 in guiding nasal tubes (not shown) along the sides of a patient's face, thus keeping the nasal tubes conveniently out of the way and in suitable order to minimize patient discomfort from their presence.

According to the description hereinabove, there is provided by the present invention an improved endotracheal tube holder offering numerous advantages over the prior art. The description is of a presently preferred embodiment of the invention and is not intended to be limiting on the scope of the invention as a wide range of design variations are believed possible within the scope of the invention described. Accordingly, the invention is intended to be construed as broadly as permitted by the scope of the claims appended hereto.

I claim:

1. In an endotracheal tube holder apparatus for securing an endotracheal tube in the operative position thereof in the airway of a patient, the combination comprising:
    a rigid face plate means adapted to be retained adjacent the mouth and jaw of such a patient;
    said face plate means including a rigid support portion which projects outwardly thereof and is adapted to project outwardly with respect to the mouth of such a patient;
    an elongated tube platform portion affixed to said face plate means centrally thereof and adapted for receiving one end of an endotracheal tube in the operative position thereof passing through the mouth and into the airway of such a patient;
    said elongated platform portion having an inner end portion which projects inwardly of said face plate means and is adapted to reside within the oral cavity of a patient and thereby provide a bite block for such a patient, and a resiliently flexible outer end portion located outwardly of said inner end portion and projecting outwardly of said face plate means with said outer end portion being affixed with respect to and supported by said rigid support portion; said outer end portion including resiliently flexible tube restraining clamp means which are cooperable with said rigid face plate means for fixedly retaining such an endotracheal tube with respect to said rigid face plate means;
    said face plate means including respective left and right frame portions which are rigidly affixed with respect to and extend laterally in opposite directions from said rigid support portion and are engageable with respective left and right portions of the face of such a patient;
    a harness means cooperable with said frame portions for securing said endotracheal tube holder with respect to the head of such a patient;
    said harness means comprising an elongated non-extensable head band adapted to generally horizontally encompass the head of such a patient and a non-extensible overhead strap affixed to said head band adapted to extend over the head of such a patient from side to side; and
    a non-extensible retaining strap means cooperable with said frame portions and said harness means for fixedly retaining said endotracheal tube holder on the face of such a patient.

2. The combination as claimed in claim 1 additionally including tube receiving channel means extending substantially throughout the longitudinal extent of said platform portion.

3. The improvement as claimed in claim 2, wherein said outer end portion is transversely flexible with respect to adjacent portions of the rigid face plate assembly.

4. The combination as claimed in claim 3 wherein said resiliently flexible clamp means includes a pair of overlapping resiliently flexible elongated tabs which are maintained in tension by engagement with said rigid face plate means in a manner to cross over and engage such an endotracheal tube disposed in said channel to thereby fixedly retain the tube within said tube receiving channel.

5. The combination as claimed in claim 1 wherein said left and right frame portions define respective left and right open areas adjacent said platform portion and said open areas including area portions which are adapted to open to the left and right sides, respectively, of such a patient's mouth to permit access to the mouth of such patient on laterally opposite sides of said platform portion.

6. The combination as claimed in claim 1, additionally including nasal tube clamp means mounted on said left and right frame portions for retaining respective left and right nasal tubes in the operative positions thereof.

* * * * *